US012755818B2

(12) United States Patent
Nouira et al.

(10) Patent No.: US 12,755,818 B2
(45) Date of Patent: Oct. 6, 2026

(54) DATA SECURITY IN AN ELECTRONIC DATA CAPTURE SYSTEM

(71) Applicant: Medidata Solutions, Inc., New York, NY (US)

(72) Inventors: Marouane Nouira, New York, NY (US); Matthew Riley, New York, NY (US); Sabrina Xu, New York, NY (US)

(73) Assignee: Medidata Solutions, Inc., New York, NY (US)

(*) Notice: Subject to any disclaimer, the term of this patent is extended or adjusted under 35 U.S.C. 154(b) by 0 days.

(21) Appl. No.: 19/014,716

(22) Filed: Jan. 9, 2025

(65) Prior Publication Data

US 2026/0196313 A1 Jul. 9, 2026

(51) Int. Cl.
*G16H 10/20* (2018.01)
*G16H 10/60* (2018.01)

(52) U.S. Cl.
CPC ............. *G16H 10/20* (2018.01); *G16H 10/60* (2018.01)

(58) Field of Classification Search
CPC ....... G16H 10/20; G16H 10/60; H04W 12/02; G06F 21/60; G06F 21/62
USPC .......................................................... 705/2, 3
See application file for complete search history.

(56) References Cited

U.S. PATENT DOCUMENTS 11,127,403 B2 9/2021 Medalion et al.
11,736,564 B1 8/2023 Jain et al.
2006/0259783 A1* 11/2006 Work ..................... G16H 10/20 713/189
2020/0285771 A1* 9/2020 Dey .................... G06F 21/6272
2021/0125615 A1* 4/2021 Medalion ................ G10L 15/26
2021/0151136 A1* 5/2021 Lee ........................ G16H 10/20
2023/0004675 A1* 1/2023 Amar ...................... G06F 21/64
2023/0128136 A1 4/2023 Sahu et al.
2024/0274245 A1* 8/2024 Ikeguchi ................ G16H 10/20
2024/0289492 A1 8/2024 Gupta et al.

FOREIGN PATENT DOCUMENTS

WO WO-2024044273 A1 * 2/2024 ............. G16H 10/20

OTHER PUBLICATIONS

Extended European Search Report in European Appln. No. 25227616.7, mailed on May 20, 2026, 11 pages.

* cited by examiner

*Primary Examiner* — Alaaeldin M. Elshaer
(74) *Attorney, Agent, or Firm* — Fish & Richardson P.C.

(57) ABSTRACT

A method implemented by a computer system for detecting personally identifiable information (PII) in clinical trial data before the clinical trial data is committed to a hardware storage device to improve data security, comprising: causing rendering of a graphical user interface for input of clinical trial data and one or more controls; receiving, through the graphical user interface, input clinical trial data; prior to committing the clinical trial data to a hardware storage device, associating, in memory, the clinical trial data associated with a pending state; upon determining that the clinical trial data does not include PII, accessing, from memory, the clinical trial data input into at least one of the one or more input portions; releasing the clinical trial data from the pending state; and committing the clinical trial data released to the hardware storage device.

20 Claims, 9 Drawing Sheets

DATA SECURITY IN AN ELECTRONIC DATA CAPTURE SYSTEM

TECHNICAL FIELD

This description generally relates to systems and methods for improving data security of clinical trial data in an electronic data capture system by using pending state indicators to delay committing the clinical trial data to memory until an absence of sensitive information is determined and then releasing the clinical trial data and committing it to memory.

SUMMARY

Implementations according to this disclosure include a method implemented by a computer system for detecting personally identifiable information (PII) in clinical trial data before the clinical trial data is committed to a hardware storage device to improve data security, comprising: causing rendering, by a computer system, of a graphical user interface with one or more input portions for input of clinical trial data and one or more controls; responsive to selection of at least one of the one or more controls, receiving, by the computer system through the graphical user interface, clinical trial data input into at least one of the one or more input portions of the graphical user interface; prior to committing the clinical trial data to a hardware storage device, associating, in memory, the clinical trial data input into at least one of the one or more input portions of the graphical user interface with a pending state; detecting, by a machine learning model, whether the clinical trial data includes PII; at least partly based on an output of the machine learning model, determining whether the clinical trial data includes PII; upon determining that the clinical trial data does not include PII, accessing, from memory, the clinical trial data input into at least one of the one or more input portions of the graphical user interface and associated with the pending state; releasing the clinical trial data from the pending state; and committing the clinical trial data released to the hardware storage device.

In some implementations, the actions include receiving, from the machine learning model, an indication that the clinical trial data does not include PII. The actions include receiving, from the machine learning model, an indication that the clinical trial data includes PII; causing rendering an overlay in the graphical user interface, with the rendered overlay displaying a notification of the detected PII and further displaying: a first prompt to confirm that the clinical trial data does not include PII, with the first prompt being juxtaposed to the notification in the overlay; and a second prompt to update the clinical trial data to not include PII, with the second prompt being juxtaposed to the notification in the overlay. The actions include receiving data confirming that the clinical trial data does not include PII. The overlay is a first overlay, the method further comprising: receiving, by the computer system through the graphical user interface, an update to the input clinical trial data; prior to committing the update to the input clinical trial data to the hardware storage device, associating, in memory, the update to the clinical trial data with a pending state indictor; causing, by the computer system, the machine learning model to detect whether the update to the input clinical trial data includes PII; when the machine learning model detects that the update to the input clinical trial data includes PII, rendering a second overlay in the graphical user interface, with the rendered second overlay displaying another notification of the detected PII and further displaying: a first prompt to confirm that the update to the clinical trial data does not include PII, with the first prompt being juxtaposed to the other notification in the second overlay; and a second prompt to update the updated clinical trial data to not include PII, with the second prompt being juxtaposed to the other notification in the second overlay; repeating steps a-d until confirmation is received that an update to the clinical trial data does not include PII or until the machine learning model detects an absence of PII, once confirmation is received that the update to the clinical trial data does not include PII or the machine learning model detects an absence of PII, committing a most recently submitted update to the input clinical trial data to the hardware storage device.

In some implementations, the machine learning model is a large language model (LLM), the method further comprising: generating a system prompt to guide the LLM to interpret input corresponding to the clinical trial data input into at least one of the one or more input portions of the graphical user interface and to provide a specified type of output; and inputting, into the LLM, the system prompt and the input corresponding to the clinical trial data input into at least one of the one or more input portions of the graphical user interface. Committing includes: creating an entry in a specified table in the hardware storage device, with data corresponding to the input clinical trial data being saved in the created entry; and creating an entry in an audit trail table to track modifications to the input clinical trial data or to data corresponding to the input clinical trial data. Committing the clinical trial data to the hardware storage device includes committing data corresponding to the clinical trial data to the hardware storage device.

In other implementations, a software development system is provided for developing software for detecting personally identifiable information (PII) in clinical trial data before the clinical trial data is committed to a hardware storage device to improve data security, the software development system comprising one or more processors, and one or more machine-readable hardware storage devices storing instructions that are executable by the one or more processors to (a) receive code that when executed performs operations comprising: causing rendering, by a computer system, of a graphical user interface with one or more input portions for input of clinical trial data and one or more controls; responsive to selection of at least one of the one or more controls, receiving, by the computer system through the graphical user interface, clinical trial data input into at least one of the one or more input portions of the graphical user interface; prior to committing the clinical trial data to a hardware storage device, associating, in memory, the clinical trial data input into at least one of the one or more input portions of the graphical user interface with a pending state; detecting, by a machine learning model, whether the clinical trial data includes personally identifiable information (PII); at least partly based on an output of the machine learning model, determining whether the clinical trial data includes PII; upon determining that the clinical trial data does not include PII, accessing, from memory, the clinical trial data input into at least one of the one or more input portions of the graphical user interface and associated with the pending state; releasing the clinical trial data from the pending state; and committing the clinical trial data released to the hardware storage device; and (b) store the code.

Other embodiments of this aspect include corresponding computer systems (e.g., a data processing system), apparatus, and computer programs recorded on one or more computer storage devices, each configured to perform the actions or operations described herein. A system of one or more computers can be configured to perform particular actions by virtue of having software, firmware, hardware, or a combination of them installed on the system that in operation causes or cause the system to perform the actions. One or more computer programs can be configured to perform particular actions by virtue of including instructions that, when executed by a data processing apparatus, cause the apparatus to perform the actions.

A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

The techniques described herein provide an electronic data capture (EDC) system that initially captures or stores (e.g., temporarily stores in memory) data in a pending state, which serves as a safeguard for data submissions within the EDC system. When users enter data, it is temporarily held in this pending state, allowing the system to perform real-time detection of sensitive information, such as, e.g., PII, before the data is released into the database and audit trail. If no PII is detected, the data is released from the pending state and securely entered into the system. If PII is identified, the system notifies the user, giving them the opportunity to correct the data or confirm it before allowing the submission. This system effectively acts as a shield, preventing unauthorized or sensitive information from being logged. The holding of the data in a pending state (and only committing the data to memory upon confirmation of an absence of sensitive information) improves memory and processing resource allocation by not storing data (containing sensitive information) that will then need to be subsequently modified, e.g., in an audit trail. This modification of the data and/or of the audit trail consumes processing resources that are conserved if the data is cleansed (e.g., by the sensitive information being removed) prior to committing to memory (e.g., a data store or random access memory). That is, the system described herein consumes few processing resources by simply committing data not including sensitive information to memory, relative to the amount of resources required to commit data including sensitive information to memory and then needing to modify that data (or the audit trail), e.g., repeatedly. The techniques described herein also reduce the consumption of memory resources. This is because is requires less memory to store data a single time (which is what happens when data does not contain sensitive information), relative to the amount of memory required to save data including sensitive information and then save versions of that data with the sensitive information removed or modified.

Additionally, the data processing system described herein generates software to perform the functionality of a pending state marker, a prompter, a PII Prevention ML Engine, a PII detector and a data committer, as described herein. This software includes new code that allows a computer processor to process data more efficiently, because the techniques described herein eliminate having to access stored data (including PII) multiple times to modify or delete an audit trail for that data or to modify the data itself. Instead, the data is first checked for PII, and only when it is confirmed that the data does not include PII, then data it committed to memory—eliminating the need to access the data subsequently to modify it or its associated audit trail. As such, a technical problem has been solved (e.g., how to process data more efficiently), since the technical effects produced clearly go beyond the normal physical effects produced by an ordinary piece of software.

The EDC system that holds data in a pending state addresses key technical problems, as follows. First, this EDC system shields the database and audit trail from unverified PII, reducing the risk of compliance breaches. Second, this EDC system automates PII checks in real-time before data is released, minimizing the need for costly manual reviews. Third, this EDC system ensures only compliant, secure data is stored, facilitating adherence to regulatory standards such as General Data Protection Regulation (GDPR) and Health Insurance Portability and Accountability Act (HIPAA). By acting as a filter before data enters the system, the techniques described herein enhance data security, integrity, and compliance within EDC systems.

The techniques described herein offer several advantageous effects in storing PII within an EDC system, as follows. First, the techniques described herein provide for increased efficiency. Unlike current systems, which often rely on manual reviews after PII has been entered, the techniques described herein automate the detection process in real time. This reduces the need for labor-intensive checks and significantly decreases the time required to ensure data integrity and compliance. Second, the techniques described herein improve accuracy in detecting PII. By introducing real-time PII detection in the pending state, these techniques minimize the risk of human error, which is common in manual reviews. The system ensures that PII is consistently identified before data is stored, leading to greater accuracy in data handling. Third, data security is enhanced. The pending state workflow acts as a shield, preventing unverified or sensitive data from entering the database or audit trail. This proactive measure ensures that PII is not inadvertently stored, reducing the risk of compliance breaches and improving overall data security. Fourth, regulatory compliance is increased. The automated PII detection and prevention mechanisms help ensure that data entry complies with stringent privacy regulations, such as GDPR and HIPAA. This reduces the risk of penalties and audits related to the mishandling of sensitive information. Fifth, the speed of data processing is increased. By automating the PII detection process and releasing safe data into the database without manual intervention, the techniques described herein accelerate data processing. This speed is crucial in environments like clinical trials, where data must be handled quickly and efficiently. Sixth, consistency across data sources is achieved.

These techniques ensure that PII is handled uniformly across different data entry points and forms, providing a consistent level of protection and reducing the risk of gaps in data security. Compared to existing systems, which often suffer from inefficiencies, human error, and inconsistent PII handling, the techniques described herein offer a faster, more accurate, and secure approach to managing PII in EDC systems.

The details of one or more embodiments of the subject matter of this specification are set forth in the accompanying drawings and the description below. Other features, aspects, and advantages of the subject matter will become apparent from the description, the drawings, and the claims.

DETAILED DESCRIPTION

Figure 1:
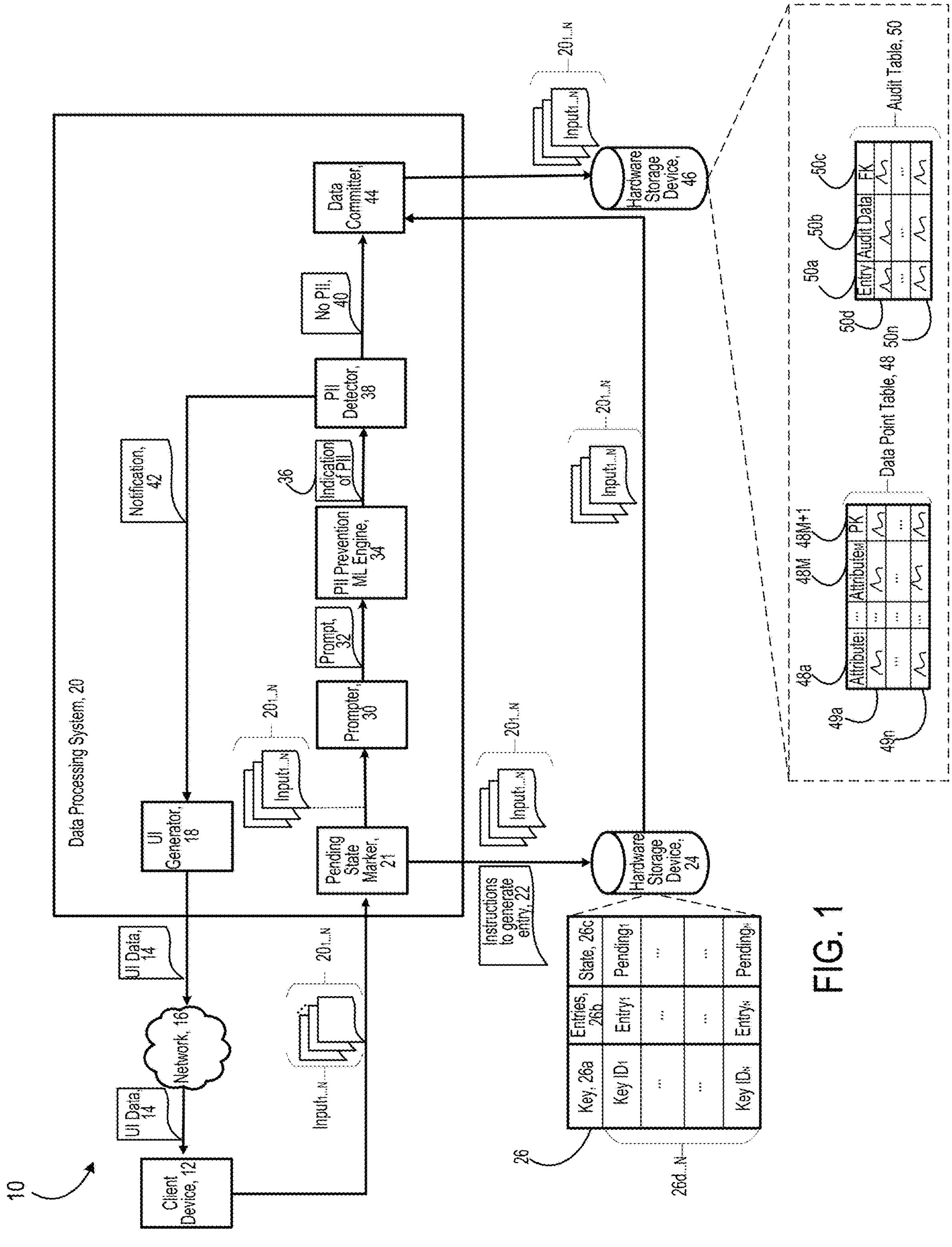
FIG. 1 shows a data processing environment for improving data security.

Managing PII presents a significant challenge for EDC systems used in clinical trials. PII includes data that can directly or indirectly identify an individual, such as names, birthdates, social security numbers, or medical records. Regulatory bodies such as the Federal Drug Administration (FDA), European Medicines Agency (EMA), and GDPR require stringent controls over the handling, storage, and transmission of PII to protect patient privacy and ensure compliance.

When PII is not adequately checked before it is entered into the database, this degrades data security. This means that clinical trial data, including sensitive information such as patient names, addresses, or other PII, can be inadvertently entered by users without real-time verification. Once this data is saved in the database, it becomes part of the audit trail.

The audit trail, designed to track every change made to the data, captures and preserves every action and entry, including any PII that may have been mistakenly entered. Once PII is logged into the audit trail, it cannot be easily modified or removed due to strict regulatory requirements. This leads to several major problems. First, this reduces data integrity and increases privacy risks. Sensitive information is permanently recorded in the system, even if it is later identified as inappropriate or incorrect. This creates privacy risks and compliance challenges, especially in jurisdictions with stringent data protection laws like the GDPR. Second, once PII is logged into the audit trail, rectifying this issue can be costly (in terms of computation resources required to do so) and time-consuming. Modifying or removing audit trail entries typically requires complex, post-hoc procedures that must be fully documented and justified to satisfy regulatory requirements. This process is not only resource-intensive but also prone to errors, increasing the risk of non-compliance. The techniques described herein improve data security by detecting PII before it enters the system and is captured in an audit trail. The techniques described herein also improve accuracy in detecting PII based on training a machine learning (ML) model to detect PII based on both values of the data and the structure of the data.

In particular, the techniques described herein have identified and solved the following technical problems of unverified PII entry (wherein PII is not checked before being entered into the database, leading to sensitive data being inadvertently logged and saved), immutable audit trails (once PII is entered, it becomes part of the audit trail, which cannot be easily modified, creating compliance and privacy risks), manual review bottlenecks (many systems rely on manual processes to detect PII post-entry, which is time-consuming, error-prone, and costly), inconsistent PII handling (different data sources and forms may handle PII differently, resulting in gaps in data security and privacy protections), and compliance risks (adhering to strict data protection laws like GDPR and HIPAA is challenging, especially when PII is inadvertently captured and stored).

Referring to FIG. 1, data processing environment 10 is shown. Data processing environment 10 includes client device 12, network 16 and data processing system 20 (e.g., an EDC system). In this example, data processing environment 10 includes an environment for detecting whether input data, such as clinical trial data, includes PII. In this example, data processing system 20 includes user interface (UI) generator 18 for providing or generating UI data 14 that when rendered on client device 12, causes client device 12 to display one or more user interfaces. Data processing system 20 also includes pending state marker 21 for receiving input data and storing (temporarily storing) the input data with a pending state indicator (also referred to herein as a pending state) to allow a machine learning engine to detect whether the input data includes PII, and if so to correct it, prior to committing that input data to a hardware storage device. Data processing system 20 also includes prompter 30 for generating a prompt to be transmitted to PII prevention ML engine 34. PII prevention ML engine 34 includes a ML model for detecting PII and for outputting to PII detector 38 an indication 36 of whether the input data includes PII or not. In turn, PII detector 38 either sends a notification 42 of PII or, if there is no indication of PII, transmits message 40 to data committer 44 for actually committing the input data (or a copy of the input data) to a hardware storage device, e.g., hardware storage device 46. In this example, UI generator 18 receives notification 42. Based on received notification 42, UI generator 18 generates one or more additional UIs that prompt a user to either specify that the input does not include PII or to correct the PII, as described herein. Data processing environment 10 also includes hardware storage devices 24 and 46 for storing data, structured data, and tables as described herein.

In operation, client device 12 renders one or more user interfaces in accordance with UI data 14. These user interfaces include input portions for a user to input (or otherwise specify) input data $\mathbf{20}_{1 \ldots N}$ (including, e.g., clinical trial data) into data processing system 20. In this example, client device 12 transmits input data $\mathbf{20}_{1 \ldots N}$ to data processing system 20 and input data $\mathbf{20}_{1 \ldots N}$ is received by pending state marker 21. Pending state marker 21 is configured to identify that input data $\mathbf{20}_{1 \ldots N}$ needs to be checked for PII, prior to committing input data $\mathbf{20}_{1 \ldots N}$ to memory (e.g., in hardware storage device 46). As such, pending state marker 21 transmits, to hardware storage device 24, input data $\mathbf{20}_{1 \ldots N}$ and instructions 22 to generate an entry in pending state table 26 for input data $\mathbf{20}_{1 \ldots N}$.

In this example, hardware storage device 24 stores pending state table 26 to store and/or to indicate which data is being temporarily stored, e.g., pending results of PII detection on the data. Pending state table 26 includes columns 26*a*, 26*b*, 26*c* specifying a key (e.g., a unique identifier), the input data itself (or an entry representing the input data) and a state of that input data. In this example, input data includes or is associated with a key that uniquely identifies input data. Pending state table 26 includes rows 26*d* . . . N, e.g., with a row corresponding to input data received as part of a particular request or transmission sent to data processing system 20. In this example, row 26*d* is for input data $\mathbf{20}_{1 \ldots N}$. In this example, $\text{entry}_1$ (e.g., entry in a cell defined by row 26*d* and column 26*b*) includes a pointer to a memory location in hardware storage device 24 that stores input $\mathbf{20}_{1 \ldots N}$. In this example, key $\text{ID}_1$ specifies a value of a key included in input data $\mathbf{20}_{1 \ldots N}$. If input data $\mathbf{20}_{1 \ldots N}$ does not include or otherwise specify a value of a key, pending state marker 21 transmits to hardware storage device 24 instructions to populate the cell defined by column 26*a* and row 26*d* with a timestamp specifying the time at which input data $\mathbf{20}_{1\ldots N}$ was received by data processing system 20. The value of the key ID allows input data $\mathbf{20}_{1\ldots N}$ to be identified and retrieved at a subsequent time, e.g., a time in which it is being committed to memory.

Pending state marker 21 then transmits input data $\mathbf{20}_{1\ldots N}$ to prompter 30. Prompter 30 generates prompt 32, which includes input data $\mathbf{20}_{1\ldots N}$ and a request to detect whether input data $\mathbf{20}_{1\ldots N}$ includes PII. Prompter 30 transmits prompt 32 to PII prevention ML engine 34, which applies one or more (trained) machine learning models to input data $\mathbf{20}_{1\ldots N}$ to detect whether input data $\mathbf{20}_{1\ldots N}$ includes PII. When PII prevention ML engine 34 detects PII, PII detector 38 generates notification 42, as previously described. When PII prevention ML engine 34 does not detect PII, PII detector 38 transmits message 40 to data committer 44. Message 40 specifies that input data $\mathbf{20}_{1\ldots N}$ does not include PII. Message 40 identified input data $\mathbf{20}_{1\ldots N}$ through the key associated with input data $\mathbf{20}_{1\ldots N}$. This key was included in or specified by input data $\mathbf{20}_{1\ldots N}$ that was received by prompter 30, and, in turn, was included in prompt 32 and message 40.

Upon receipt of message 40, data committer 44 transmits, to hardware storage device 24, a request for input data $\mathbf{20}_{1\ldots N}$. The request includes the key associated with input data $\mathbf{20}_{1\ldots N}$. In response, hardware storage device 24 transmits input data $\mathbf{20}_{1\ldots N}$ to data committer 44, which in turn, transmits input data $\mathbf{20}_{1\ldots N}$ to hardware storage device 46 for storage.

Hardware storage device 46 includes data point table 48 and audit table 50. Data point table 48 includes a table for storing input data $\mathbf{20}_{1\ldots N}$, e.g., by each cell in data point table 48 specifying or storing an individual piece of data, which may be referred to as an attribute. As such, data point table 48 includes columns 48*a* . . . 48M corresponding to various attributes of input data. Data point table 48 also includes column 48M+1, which specifies a primary key (PK) that links or otherwise points to a particular row in audit table 50 thereby enabling data processing environment 10 to specify an audit trail for the various received input data.

Data point table 48 also includes rows 49*a* . . . 49*n* with each row corresponding to input data received from a client device. In this example, input data $\mathbf{20}_{1\ldots N}$ is stored in row 49*a* of data point table 48. In this example, data committer 44 includes data processing rules and/or a parser to identify values of various attributes of input data $\mathbf{20}_{1\ldots N}$ and to store values of those attributes in appropriate cells for row 49*a*. A cell in data point table 48 includes a particular entry defined by a particular row and a particular column in data point table 48. In another example, data committer 44 may store input data $\mathbf{20}_{1\ldots N}$ in hardware storage device 46 in association with a primary key for accessing a particular row in audit table 50.

Audit table 50 includes columns 50*a*, 50*b*, 50*c* and rows 50*d* . . . 50*n*. In this example, column 50*a* includes data specifying information about the particular entry, for example, a timestamp. Column 50*b* specifies the audit data, including, e.g., data specifying one or more modifications to input data. Column 50*c* specifies a foreign key (FK) for a primary key specified by column 48M+1 in data point table 48. Through use of the foreign keys specified in column 50*c*, data processing environment 10 can identify a corresponding primary key in data point table 48, thereby enabling data processing environment 10 to identify which audit data corresponds to a row in data point table 48. Audit table 50 includes rows 50*d* . . . 50*n* specifying audit data for various received input data. In this example, row 50*d* includes audit data for input data $\mathbf{20}_{1\ldots N}$. In this example, audit data includes data specifying the time at which data for input data $\mathbf{20}_{1\ldots N}$ was committed to data point table 48 and further specifies any other updates or modifications that may have been made to that data after the data was originally committed. In some examples, data committer 44 transmits to hardware storage device 46 the audit data associated with input data $\mathbf{20}_{1\ldots N}$.

In a variation of FIG. 1, data processing system 20 is or includes a software development system for generating or receiving code to perform the foregoing described functionality of the pending state marker 21, the prompter 30, the PII Prevention ML engine 34, the PII Detector 38 and the Data Committer 44.

PII prevention ML engine 34 includes a machine learning model. There are various types of machine learning models, including, e.g., a generative artificial intelligence (AI) model having one or more large language models (LLMs). Example LLMs include models having one or more generative pre-trained transformers (GPTs), such as those implemented using one or more artificial neural networks.

Generally, machine learning can encompass a wide variety of different techniques that are used to train a machine to perform specific tasks without being specifically programmed to perform those tasks. The machine can be trained using different machine learning techniques, including, for example, supervised learning, unsupervised learning, and reinforcement learning. In supervised learning, inputs and corresponding outputs of interest are provided to the machine. The machine adjusts its functions in order to provide the desired output when the inputs are provided. Supervised learning is generally used to teach a computer to solve problems in which are outcome determinative, for example, the training set may be used to train the trained machine learning model to detect PII. In contrast, in unsupervised learning, inputs are provided without providing a corresponding desired output. Reinforcement learning describes an algorithm in which a machine makes decisions using trial and error. Feedback informs the machine when a good choice or bad choice is made. The machine then adjusts its algorithms accordingly. For example, the trained learning model may be embodied as a generalized linear model (GLM). Different types of generalized linear models may be appropriate in various scenarios. A zero-inflated negative binomial generalized linear regression may be used because it models a discrete count of events (such as conversions) occurring in a given time period.

In another example, the trained learning model may be embodied as an artificial neural network. Artificial neural networks (ANNs) or connectionist systems are computing systems inspired by the biological neural networks that constitute animal brains. An ANN is based on a collection of connected units or nodes, called artificial neurons. Each connection, like the synapses in a biological brain, can transmit a signal from one artificial neuron to another. An artificial neuron that receives a signal can process it and then signal additional artificial neurons connected to it.

In common ANN implementations, the signal at a connection between artificial neurons is a real number, and the output of each artificial neuron is computed by some non-linear function of the sum of its inputs. The connections between artificial neurons are called 'edges'. Artificial neurons and edges may have a weight that adjusts as learning proceeds (for example, each input to an artificial neuron may be separately weighted). The weight increases or decreases the strength of the signal at a connection. Artificial neurons may have a threshold such that the signal is only sent if the aggregate signal crosses that threshold. The transfer functions along the edges usually have a sigmoid shape, but they may also take the form of other non-linear functions, piecewise linear functions, or step functions. Typically, artificial neurons are aggregated into layers. Different layers may perform different kinds of transformations on their inputs. Signals travel from the first layer (the input layer), to the last layer (the output layer), possibly after traversing the layers multiple times.

In general, a neural network is trained using a supervised learning technique based on training data, wherein the neural network is configured to receive training data as input (e.g., input data records) and to process the input to generate an output, e.g., that specifies whether PII is detected. In this example, the neural network includes a plurality of artificial neurons that are connected through edges and are aggregated into a plurality of neural network layers comprising at least an input layer and an output layer, wherein each of the edges is configured to transmit a signal from one artificial neuron to another artificial neuron, and wherein an output of each of the plurality of artificial neurons is computed based on inputs of the artificial neuron in accordance with a plurality of weights. In this example, new data is processed using the plurality of artificial neurons in the trained neural network in accordance with the values of the plurality of weights to detect PII, wherein the artificial neurons in the input layer are configured to receive the new data as input and the artificial neurons in the output layer are configured to generate a new output that specified whether PII is detected.

Figure 2:
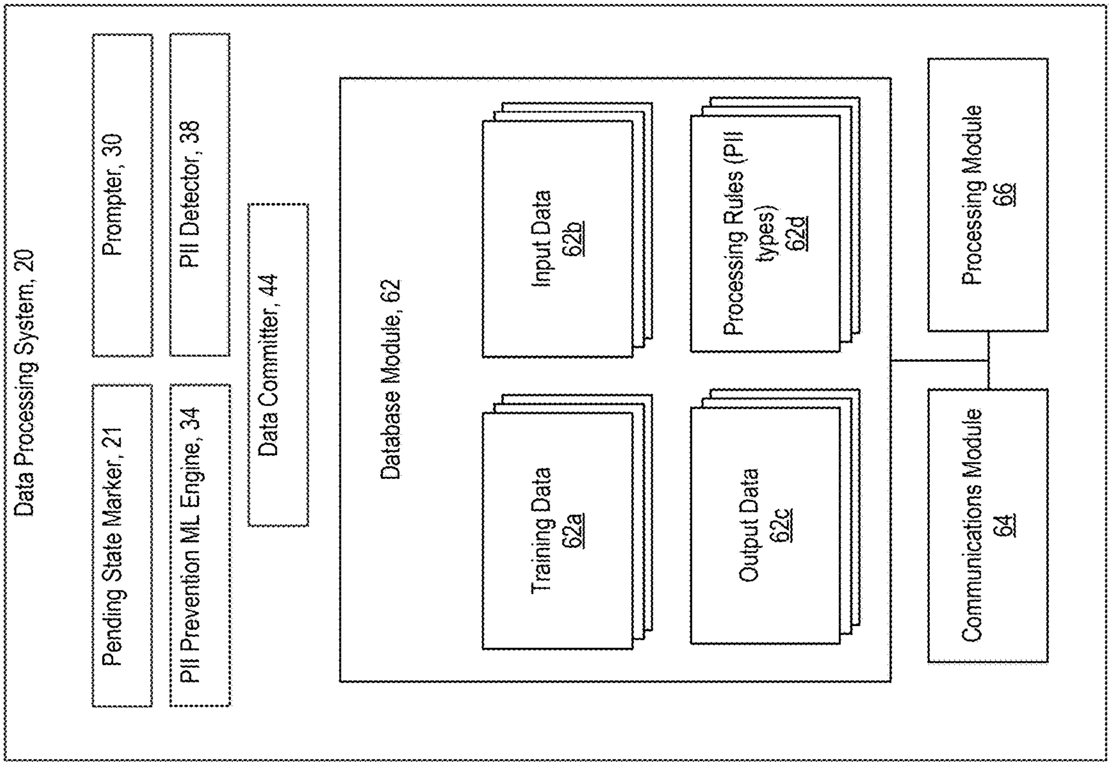
FIG. 2 shows an example data processing system for improving data security.

FIG. 2 shows various aspects of the data processing system 20. In general, the data processing system 20 includes several operation modules that perform particular functions related to the operation of the data processing system 20. For example, the data processing system 20 includes pending state marker 21, prompter 30, PII prevention ML engine 34, PII detector 38, and data committer 44, as previously described. Further, the data processing system 20 includes a database module 62, a communications module 64, and a processing module 66. The operation modules can be provided as one or more computer executable software modules, hardware modules, or a combination thereof. For example, one or more of the operation modules can be implemented as blocks of software code with instructions that cause one or more processors of the data processing system 20 to execute operations described herein. In addition or alternatively, one or more of the operation modules can be implemented in electronic circuitry such as, e.g., programmable logic circuits, field programmable logic arrays (FPGA), or application specific integrated circuits (ASIC).

The database module 62 maintains information related to detecting PII using the PII prevention ML engine 34.

As an example, the database module 62 can store training data 62*a* for training or prompting the PII prevention ML engine 34. In some implementations, the training data 62*a* can include examples of PII in clinical trial documents, such as those previously generated by the data processing system 20 and/or those manually produced by one or more human users. For instance, the training data 62*a* can include documents describing clinical trial protocols, informed consent forms, clinical study reports, and/or any other documents that facilitates the performance of a clinical trial.

As another example, the database module 62 can store input data 62*b* that is used as an input to the PII prevention ML engine 34. As an example, the input data 62*b* can include commands or instructions provided by a user, including information regarding a particular desired output of the data processing system 20, information input into a graphical user interface, and so forth. For instance, the input data 62*b* can include information regarding a user participating in the clinical trial (e.g., symptoms or medications being taken), the subject of the clinical trial (e.g., the intervention that is being tested), the types of clinical trial that is to be performed (e.g., the "phase" of the clinical trial), the intended audience of the document (e.g., a particular government agency), and/or any other information regarding the clinical trial.

Further, the input data 62*b* can include information retrieved by the data processing system 20 in support of a clinical trial. As an example, the input data 62*b* can include data retrieved from one or more drug information databases (e.g., information regarding a drug's composition, interactions between drugs, dosage of drugs, indications for use, side effects, etc.).

As another example, the input data 62*b* can include data retrieved from one or more medical or scientific journals. For instance, the input data 62*b* can include one or more articles or other publications describing the use, safety, and/or efficacy of certain drugs or other medical interventions.

As another example, the input data 62*b* can include data regarding one or more existing clinical trial protocols. For instance, the input data 62*b* can include data regarding names and other information of users who participated in a clinical trial, series of steps, procedures, actions, or operations that were previously performed (e.g., by clinical trial researchers) to assess the safety and/or efficacy of particular medical interventions.

As another example, the input data 62*b* can include data regarding one or more rules, regulations, and/or guidelines for performing clinical trials. For instance, the input data 62*b* can include data regarding government rules, regulations and/or guidelines (e.g., as specified by a government agency, such as the FDA). The input data 62*b* can also include data regarding institutional rules, regulations and/or guidelines (e.g., as specified by a public or private hospital).

Further, the database module 62 can store output data 62*c* generated by the PII prevention ML engine 34. As an example, the output data 62*c* can include one or more portions of content (e.g., text, images, charts, graphs, tables, etc.) specifying whether PII is detected or generated by the PII prevention ML engine 34 based on the input data 62*b*. As another example, the output data 62*c* can include one or more documents generated by the PII prevention ML engine 34 based on the input data 62*b*.

Further, the database module 62 can store processing rules 62*d* (e.g., rules specifying types of PII and for detecting PII) specifying how data in the database module 62 can be processed to detect PII using the PII prevention ML engine 34.

As an example, the processing rules 62*d* can include one or more rules for implementing, instruction tuning or prompting, and operating the PII prevention ML engine 34 to produce the output data 62*c*. For example, the one or more rules can specify that the training data 62*a* be provided to the PII prevention ML engine 34 for training or prompting (e.g., such that the PII prevention ML engine 34 can detect PII, identify trends and/or correlations between the contents of clinical trial input data and the subject matter therein, and generate new output based on those identified trends and/or correlations).

As another example, the one or more rules can specify that the input data 62*b* be provided to the PII prevention ML engine 34 (e.g., to generate output data 62*c* representing whether PII is detected).

As another example, the one or more rules can specify that the generated output data 62*c* be presented to the user and/or stored for future retrieval and/or processing (e.g., using the database module 62).

As another example, the one or more rules can specify one or more tools that facilitate the performance of particular actions by the PII prevention ML engine 34. For example, the tools can specify certain actions or operations that can be performed by the PII prevention ML engine 34 to detect PII, retrieve data and generate content based on the retrieved data, and so forth.

Example data processing techniques are described in further detail below.

As described above, the data processing system 20 also includes a communications module 64. The communications module 64 allows for the transmission of data to and from the data processing system 20. For example, the communications module 64 can be communicatively connected to the network 16 (FIG. 1), such that it can transmit data to and receive data from the client device 12 (FIG. 1). Information received from the client device 12 can be processed (e.g., using the processing module 66) and stored (e.g., using the database module 62).

As described above, the data processing system 20 also includes a processing module 66. The processing module 66 processes data stored or otherwise accessible to the data processing system 20. For instance, the processing module 66 can be used to execute one or more of the operations described herein (e.g., operations associated with the PII prevention ML engine 34).

In some implementations, a software application can be used to facilitate performance of the tasks described herein. As an example, an application can be installed on the data processing system 20 and/or client device 12. Further, a user can interact with the application to input data and/or commands to the data processing system 20, and review data generated by the data processing system 20.

Figure 3:
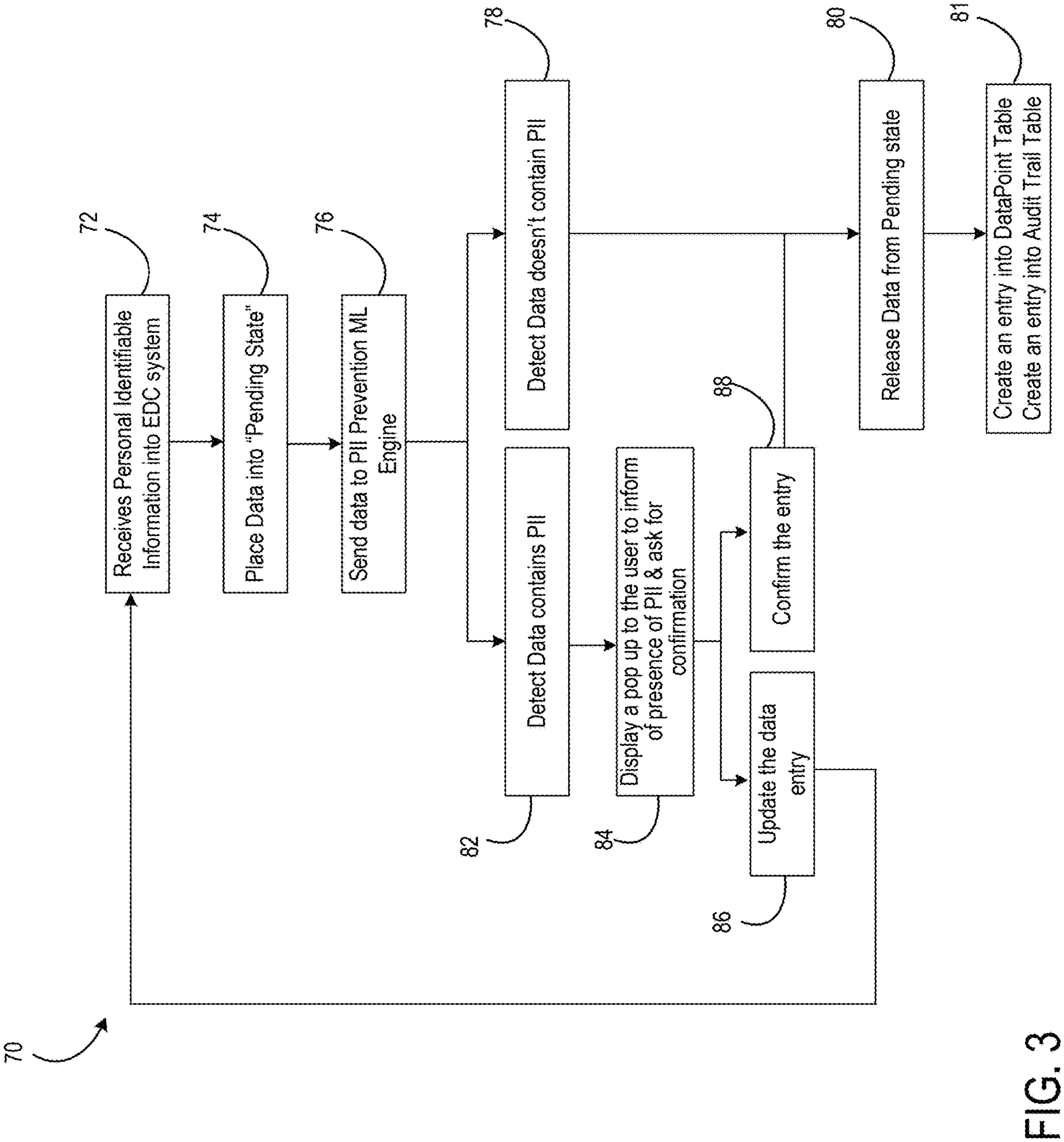
FIGS. 3 and 7 each shows example processing for improving data security.

Referring to FIG. 3, process 70 is shown for placing clinical trial data in a pending state to detect whether the clinical trial data includes PII prior to committing the clinical trial data to a hardware storage device. In operation, client device 12 receives (72) PII into an EDC system, e.g., data processing system 20. Data processing system 20 receives the entered information and places (74) that information into a pending state. While the data is placed in the pending state, data processing system 20 uses prompter 30 to transmit or send (76) the data to PII prevention ML engine 34. Using the received data, PII prevention ML engine 34 detects (78) that the data doesn't contain PII or detects (82) that the data does contain PII. When the PII prevention ML engine 34 detects that the data doesn't contain PII, data committer 44 releases (80) data from the pending state, for example, by sending to hardware storage device 24 instructions to retrieve the data and—in some examples—further instructions to remove from table 26 one or more records pertaining to the data as the data is about to be committed to hardware storage device 46 and will no longer be in a pending state. Hardware storage device 46 creates (81) an entry in data point table 48 for the received data thereby committing the data to hardware storage device 46. Hardware storage device 46 also creates an entry in audit trail table 50 for storing audit data related to the received data that is now committed to hardware storage device 46. When PII prevention ML engine 34 detects that the data contains PII, PII detector 38 transmits notification to UI generator 18, which in turn causes client device 12 to display (84) a pop up to the user to inform the user of the presence of PII and to ask for confirmation that the data does not include PII. When the data is confirmed (88) as not including PII, client device 12 transmits to PII detector 38 data specifying that there is no PII, at which point the process continues as previously described, and the data is released from the pending state. However, when the data does include PII, client device updates (86) the input data and transmits to pending state marker 21 the updated input data. The process described herein repeats until either no PII is detected or until it is confirmed that the input data does not include PII.

Figure 4:
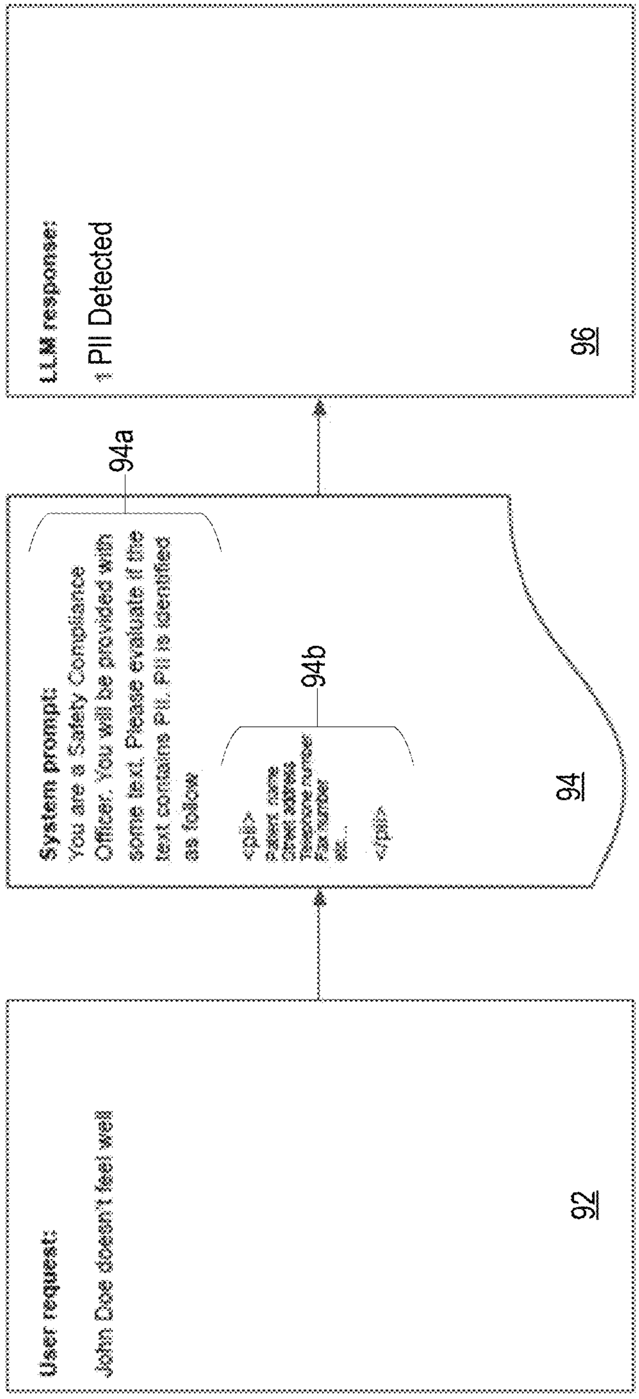
FIG. 4 shows an example input and detection of PII in the input.

Referring to FIG. 4, input data 92 is shown. Pending state marker 21 (FIG. 1) associates this input data 92 with a pending state, as described herein. Using input data 92, prompter 30 (FIG. 1) generates prompt 94 with portions 94*a*, 94*b*. Portion 94*a* instructs PII prevention ML engine 34 (FIG. 1) to evaluate input data 92 to detect whether input data 92 includes PII. Portion 94*b* specifies types of PII. Using input data 92 and prompt 94, PII prevention ML engine 34 (FIG. 1) applies a ML model and outputs response 96 specifying whether PII is detected.

In this example, prompter 30 (FIG. 1) generates detailed input instructions (e.g., prompt 94) that guide the machine learning model (e.g., an LLM) in reading, interpreting and generating the desired output. The machine learning model will be provided with the value of a text field and instructed to evaluate if the text includes PII or not. In this example, prompt 94 specifies a persona (instructions on what role the LLM should take as part of this solution), domain knowledge (a definition of PII is and what it covers (name, address, etc. . . . )), a text value (content of the text field), and an output format (0/1 (or true/false)).

Figure 5:
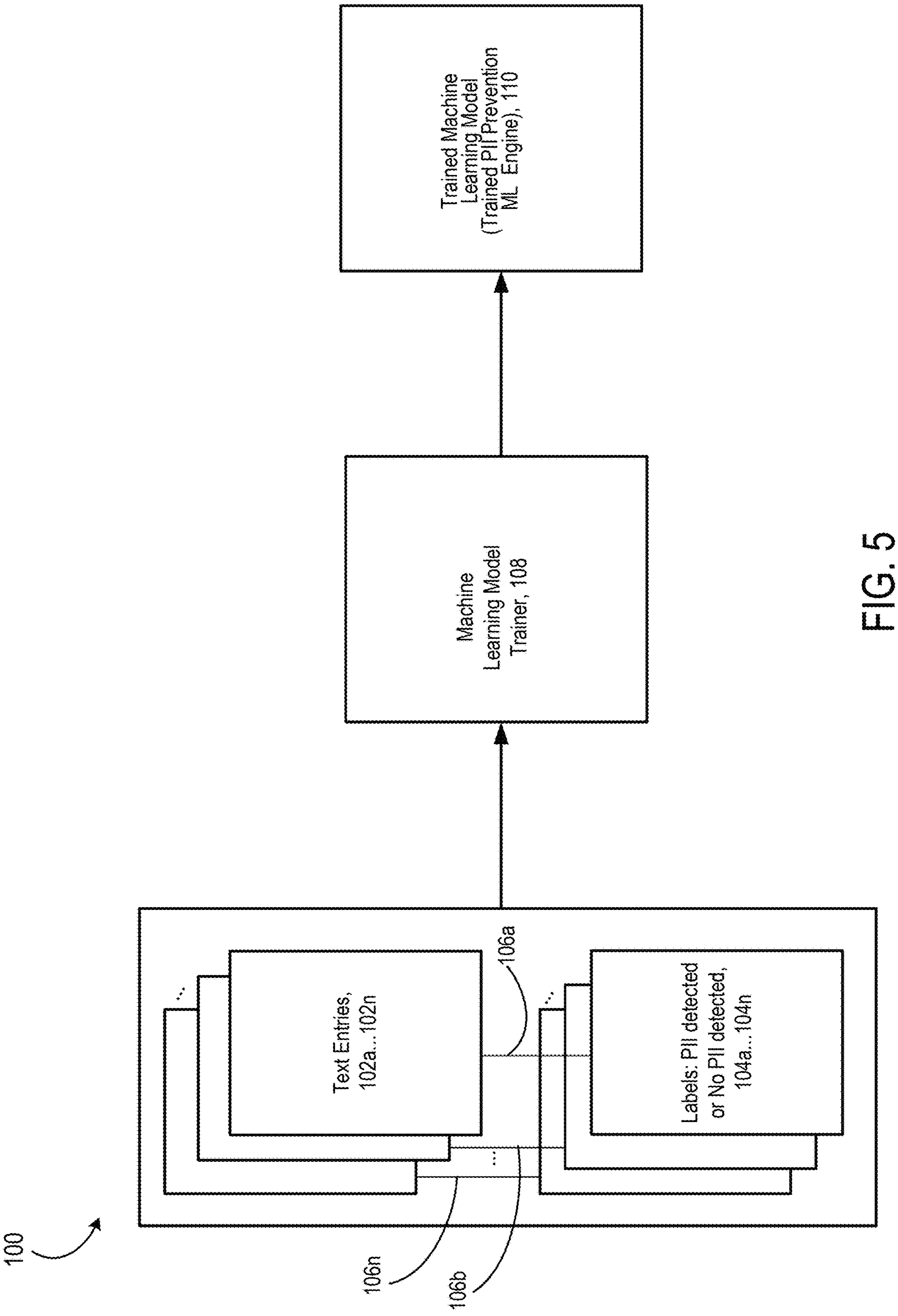
FIG. 5 depicts an example of training a machine learning system.

FIG. 5 illustrates an example of training a machine learning system. For example, training sets 102*a* . . . 102*n* input various types of input data (e.g., including text entries). The training sets 102*a* . . . 102*n* may include input data previously received for various users during a specified period of time. The training sets 102*a* . . . 102*n* are mapped via mapping structures 106*a* . . . 106*n* to labels 104*a* . . . 104*n*. A mapping structure includes a pointer or other type of structure that associates one item of data with another. The labels 104*a* . . . 104*n* specify whether a particular item of data is PII or not.

The training sets 102*a* . . . 102*n* may include any suitable number of sets of training data. Each training example in the training sets 102*a* . . . 102*n* may include contextual data specifying a name for a type of data (e.g., SSN, first name, last name, and so forth) combined with values for that particular type data. The contextual data may also include information about a structure of the data, including, e.g., whether there are hyphens in the data, whether any values are expected to be capitalized and so forth.

Using machine learning techniques as described above, a model may be trained, by the machine learning model trainer 108, to detect PII. In some implementations, the machine learning model trainer 108 may calculate numerical representations of training data (e.g., in vector form) for machine training. In some implementations, the machine learning techniques include feature extraction to build different neurons within a neural network. One or more features may translate to one or more instances of PII. For example, a particular feature may correspond to a particular type of PII, such that the strength of a feature present leads to a particular metric (e.g., indicative of PII) being determined for the corresponding events (e.g., specified types of data detected in the input data.

In some implementations, a single machine learning model may be trained. In other implementations, multiple models may be trained based training sets 102*a* . . . 102*n* mapped via mapping structures 106*a* . . . 106*n* to labels 104*a* . . . 104*n*. Once trained, the trained machine learning model is capable of receiving and processing requests. For example, given clinical trial input data, the trained machine learning model is able to detect PII. In some implementations, the trained machine learning model can filter input for whom the probability of experiencing an event (e.g., detection of PII) is below a threshold (for example, less than 50%). In some implementations, the threshold may be provided along with the training data, for example, for some events (e.g., specified types of PII) the threshold probability may be higher and for other events (e.g., other types of PII) the threshold probability may be lower.

Model Training—Historical Data Extraction and Processing

In some example, training sets 102*a* . . . 102*n* mapped via mapping structures 106*a* . . . 106*n* to labels 104*a* . . . 104*n* form training datasets. To fine-tune the PII prevention ML engine 34 (which includes a machine learning model), a small, high-quality, and diverse training dataset is used. This strategy prevents overfitting while ensuring the model performs well across different scenarios. The training dataset includes positive cases (PII detected) and negative cases (no PII detected) to provide balanced training data. The positive dataset (e.g., a training dataset with positive cases) will primarily be derived from historical data. To generate this data, data processing system 20 extracts entries from the audit trail table where PII was detected and redacted. By linking these redacted entries to internal work requests (e.g., requests to remove or redact PII), the data processing system 20 retrieves the original values submitted by users. For instance, an entry like "John Doe, 123 Main St, john.doe@example.com" will serve as the input, with the expected outcome being "PII Detected". These real-world examples form the core of the positive dataset, reflecting actual scenarios where PII was successfully managed.

To further enhance the positive dataset, the data processing system 20 generates synthetic examples of PII. These synthetic cases will cover scenarios that may not be well-represented in the historical data. By simulating diverse PII patterns, the model will gain exposure to edge cases and unusual formats, improving its robustness and generalization.

Negative cases will include entries from the audit trail where no redaction occurred, indicating that the content contained no PII. For example, entries like "Patient is stable and vitals are within normal range" will be labeled as non-PII. To enhance this dataset, the data processing system 20 generates synthetic non-PII examples, such as "The subject attended their visit on time", to ensure the model is well-trained to recognize non-sensitive content and avoid false positives.

Using the prepared dataset (as described above), the machine learning model is fine-tuned through supervised learning, where the inputs consist of text entries (both PII and non-PII cases) and the labels indicate the expected outcomes: PII detected or no PII detected.

To optimize for inference latency, data processing system 20 implements a binary classification approach, which simplifies the machine learning model's output to a straightforward 1/0 or true/false format, minimizing computational complexity and speeding up predictions. Additionally, data processing system applies model quantization techniques, reducing the precision of model weights and activations (e.g., from 32-bit floating point to 8-bit integers). This significantly decreases the model's memory footprint and computational requirements, enabling faster inference without sacrificing accuracy. Together, these optimizations ensure the model performs efficiently in real-time environments.

Figure 6A:
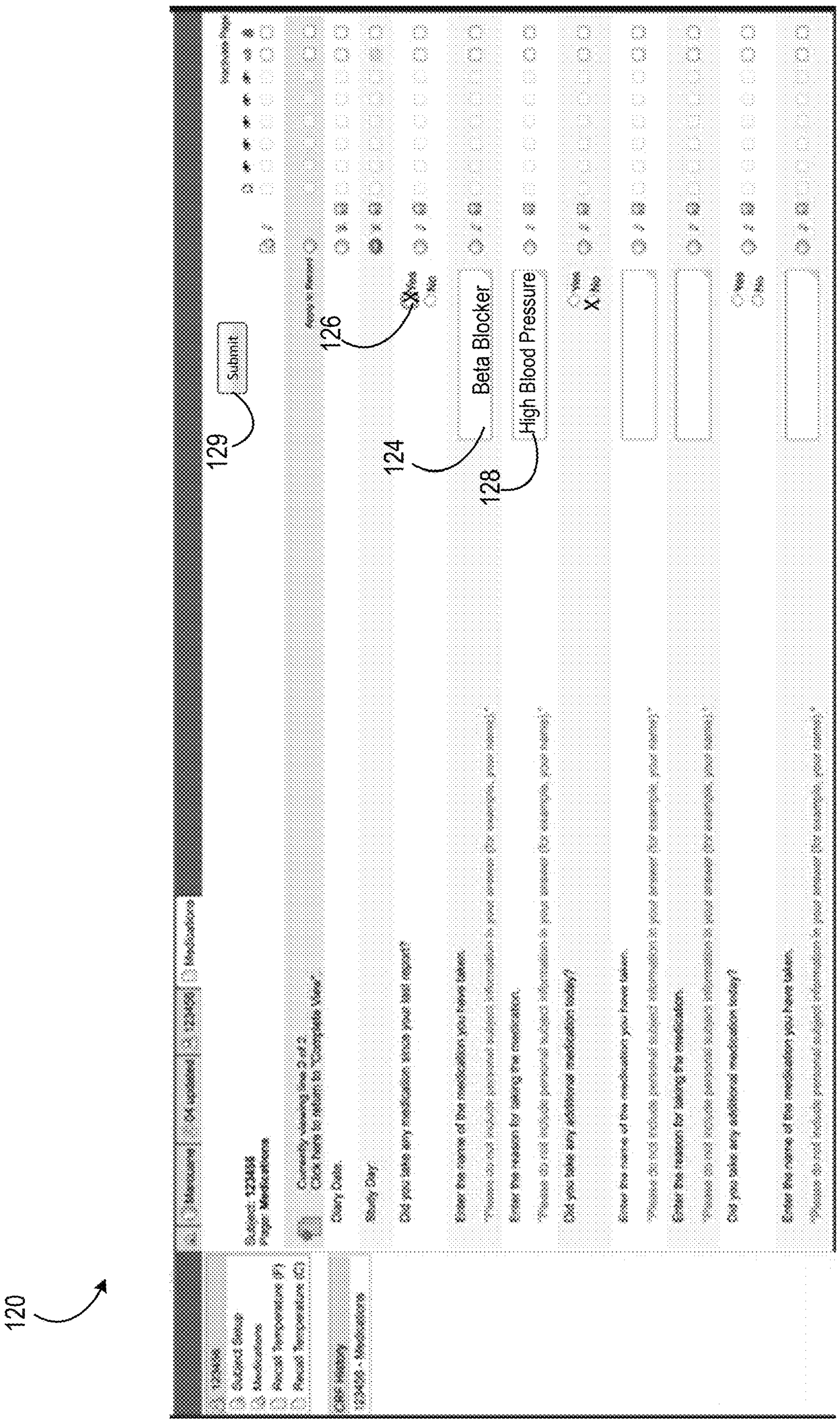
FIGS. 6A and 6B are each an example graphical user interface.

Referring to FIG. 6A, graphical user interface 120 is shown for inputting clinical trial data. Graphical user interface 120 includes control 126 and input portions 124, 128 for specifying and inputting data, including, e.g., clinical trial input data. Graphical user interface 120 also includes control 129, selection of which causes a client device to transmit to data processing system 20 (FIG. 1) data corresponding to data input into input portions 124, 128 and specified by control 126. In some examples, the data corresponding to data input into input portions 124, 128 and specified by control 126 is the data corresponding to data input into input portions 124, 128 and specified by control 126.

Figure 6B:
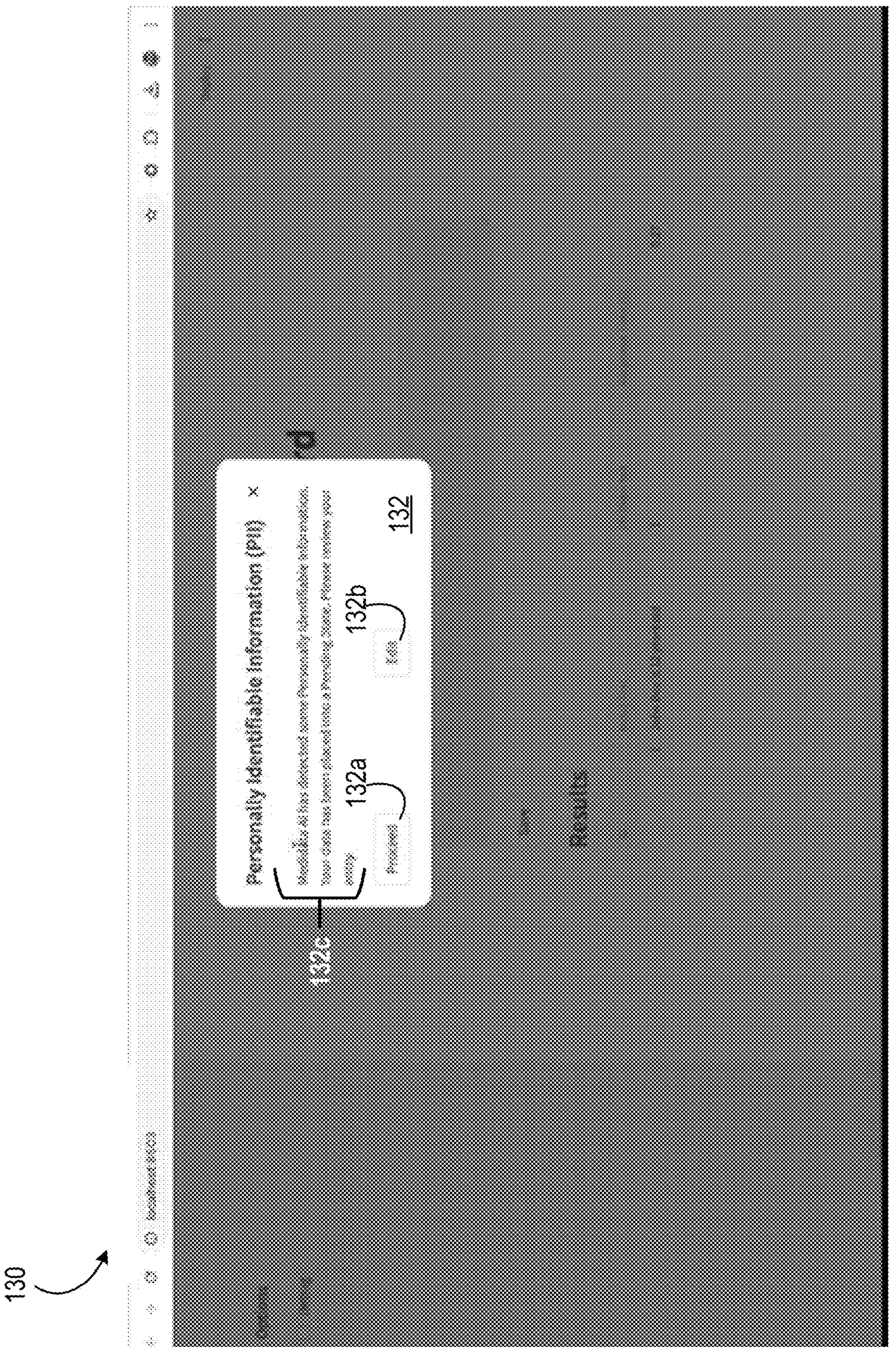

Referring to FIG. 6B, graphical user interface 130 is shown with overlay 132. In this example, overlay 132 includes an overlay to a graphical user interface, e.g., graphical user interface 120 or another graphical user interface. Overlay 132 is displayed, e.g., once PII prevention ML engine 34 detects PII, e.g., in the input data input into graphical user interface 120. Overlay 132 displays a notification of the detection of PII and prompts a user to select control 132*a* or control 132*b*. Upon selection of control 132*a*, PII detector 38 transmits to data committer 44 information specifying that no PII is detected. Upon selection of control 132*b*, a user is provided with a graphical user interface for editing the originally input data. In some examples, the provided graphical user interface is a version of graphical user interface 120, with the version displaying visual representations of the previously input data—thereby facilitating editing of this data. In this example, each of controls 132*a*, 132*b* is juxtaposed to notification 132*c* in overlay 132.

Figure 7:
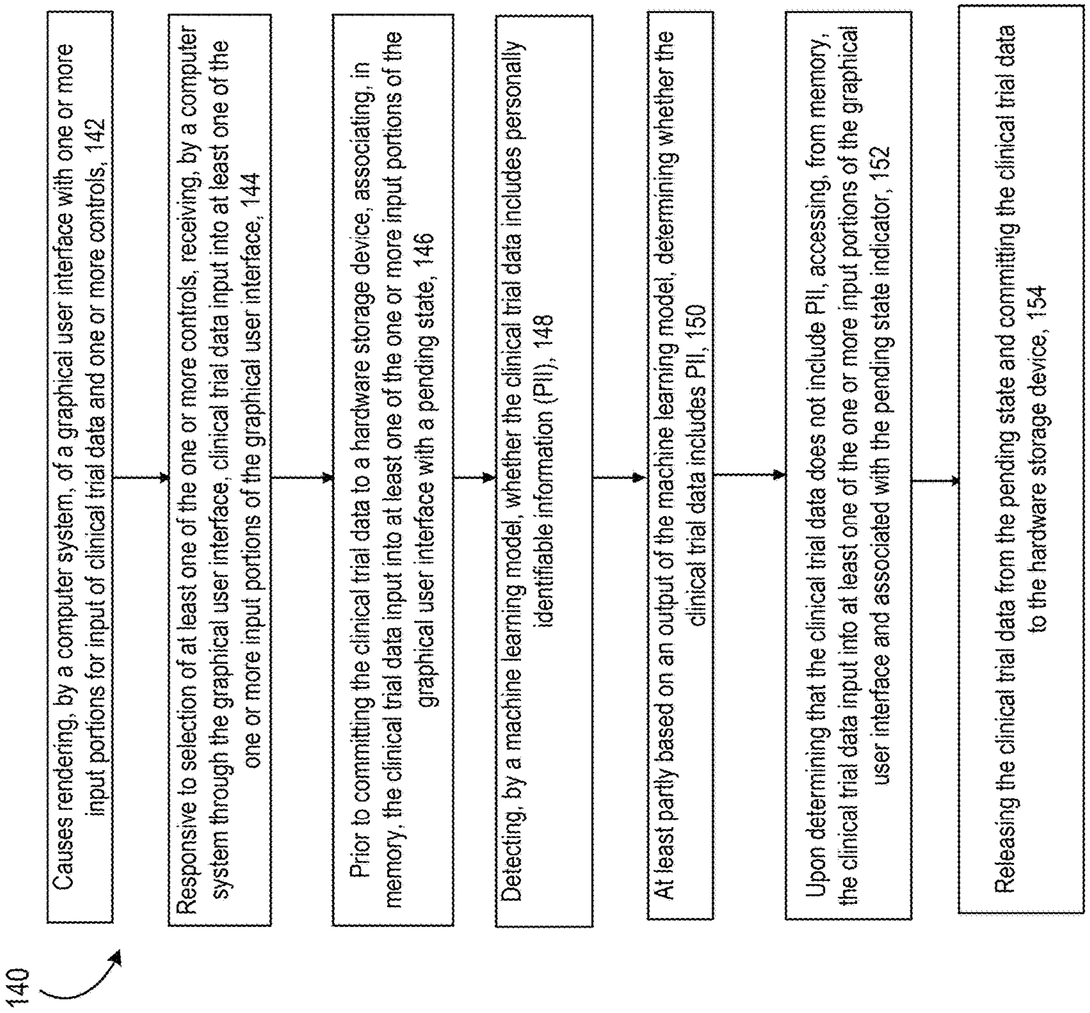

Referring to FIG. 7, process 140 is shown for detecting PII in clinical trial data before the clinical trial data is committed to a hardware storage device to improve data security. In operation, a computer system (e.g., data processing system 20 in FIG. 1) causes (142) rendering of a graphical user interface with one or more input portions for input of clinical trial data and one or more controls. Responsive to selection of at least one of the one or more controls, the computer system receives (144), the graphical user interface, clinical trial data input into at least one of the one or more input portions of the graphical user interface. Prior to committing the clinical trial data to a hardware storage device, the computer system associates (146), in memory, the clinical trial data input into at least one of the one or more input portions of the graphical user interface with a pending state. For example, the computer system may temporarily store the input clinical trial data and associate that data with a marker or other indication having a value of pending state. In another example, the computer system may identify one or more keys associated with the input clinical trial data and may store, in a table, entries specifying the one or more keys and a location in memory where the clinical trial data is stored. Then, data committer 44 (FIG. 1) can use the keys to request input data associated with the keys. And a hardware storage device that temporarily stores the input data can look-up in the table a location associated with the keys to access the input data.

Using the input data, a machine learning model detects (148) whether the clinical trial data includes PII. At least partly based on an output of the machine learning model, the computer system, or a component therein, determines (150) whether the clinical trial data includes PII. Upon determining that the clinical trial data does not include PII, the computer system accesses (152), from memory or a hardware storage device, the clinical trial data input into at least one of the one or more input portions of the graphical user interface and associated with the pending state. The computer system releases (154) the clinical trial data from the pending state, e.g., by sending instructions to a hardware storage device to commit the clinical trial data, by removing one or more entries in a table representing the clinical trial data and associated with a pending state, and so forth. The computer system commits the clinical trial data released to the hardware storage device.

Example Computer Systems

Figure 8:
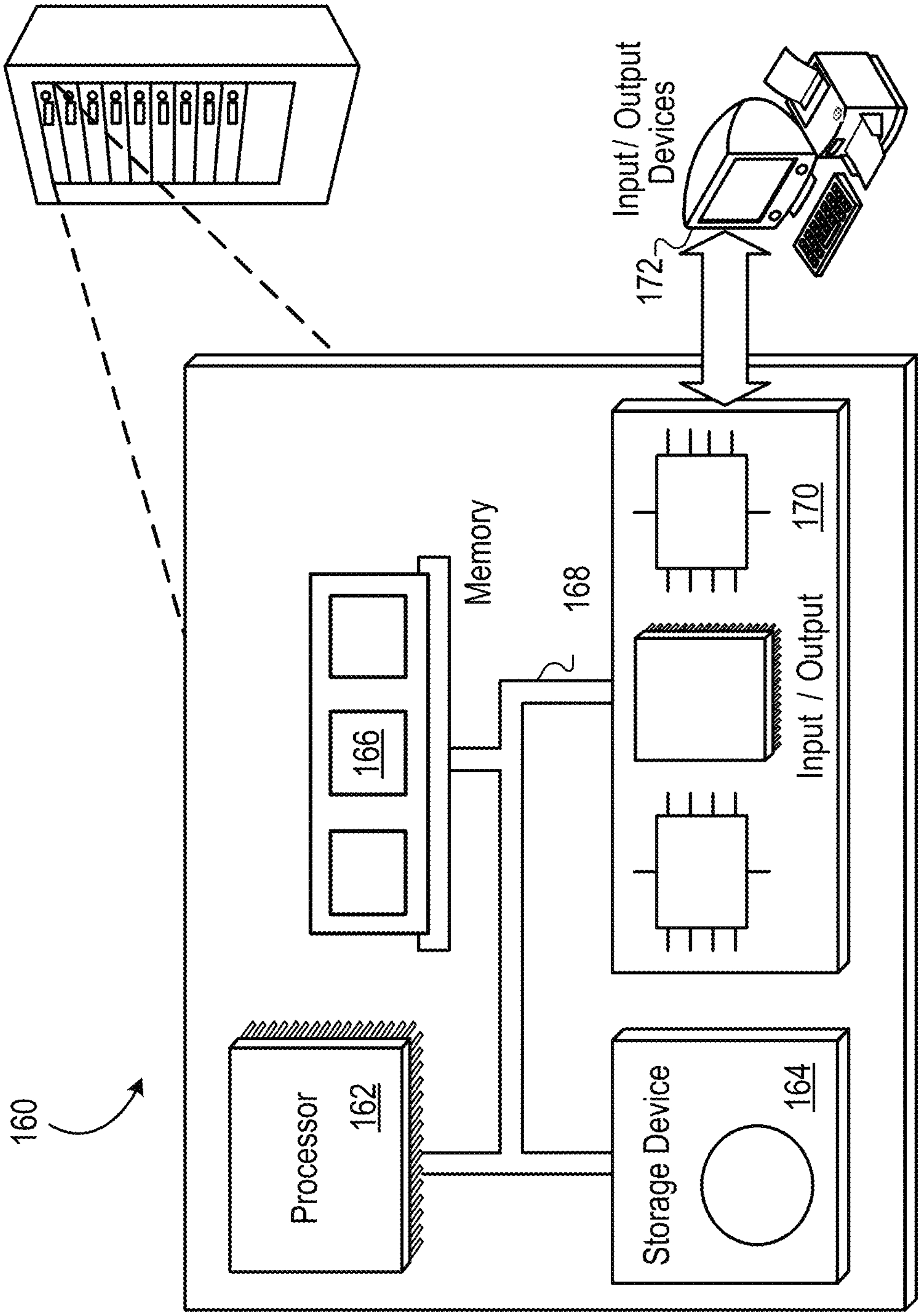
FIG. 8 depicts an example computing system, according to implementations of the present disclosure.

FIG. 8 depicts an example computing system, according to implementations of the present disclosure. The system 160 may be used for any of the operations described with respect to the various implementations discussed herein. The system 160 may include one or more processors 162, a memory 166, one or more storage devices 164, and one or more input/output (I/O) devices 172 controllable through one or more I/O interfaces 170. The various components 162, 166, 164, 170, or 172 may be interconnected through at least one system bus 168, which may enable the transfer of data between the various modules and components of the system 160.

The processor(s) 162 may be configured to process instructions for execution within the system 160. The processor(s) 162 may include single-threaded processor(s), multi-threaded processor(s), or both. The processor(s) 162 may be configured to process instructions stored in the memory 166 or on the storage device(s) 164. The processor(s) 162 may include hardware-based processor(s), each including one or more cores. The processor(s) 162 may include general purpose processor(s), special purpose processor(s), or both.

The memory 166 may store information within the system 160. In some implementations, the memory 166 includes one or more computer-readable media. The memory 166 may include any number of volatile memory units, any number of non-volatile memory units, or both volatile and non-volatile memory units. The memory 166 may include read-only memory, random access memory, or both. In some examples, the memory 166 may be employed as active or physical memory by one or more executing software modules.

The storage device(s) 164 may be configured to provide (e.g., persistent) mass storage for the system 160. In some implementations, the storage device(s) 164 may include one or more computer-readable media. For example, the storage device(s) 164 may include a floppy disk device, a hard disk device, an optical disk device, or a tape device. The storage device(s) 164 may include read-only memory, random access memory, or both. The storage device(s) 164 may include one or more of an internal hard drive, an external hard drive, or a removable drive.

One or both of the memory 166 or the storage device(s) 164 may include one or more computer-readable storage media (CRSM), including, e.g., a non-transitory computer readable medium. The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 160. In some implementations, the CRSM may include a data store that provides storage of computer-readable instructions or other information in a non-transitory format. The CRSM may be incorporated into the system 160 or may be external with respect to the system 160. The CRSM may include read-only memory, random access memory, or both. One or more CRSM suitable for tangibly embodying computer program instructions and data may include any type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 162 and the memory 166 may be supplemented by, or incorporated into, one or more application-specific integrated circuits (ASICs).

The system 160 may include one or more I/O devices 172. The I/O device(s) 172 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 172 may also include one or more output devices such as a display, LED(s), an audio output device (e.g., a speaker), a printer, a haptic output device, and so forth. The I/O device(s) 172 may be physically incorporated in one or more computing devices of the system 160, or may be external with respect to one or more computing devices of the system 160.

The system 160 may include one or more I/O interfaces 170 to enable components or modules of the system 160 to control, interface with, or otherwise communicate with the I/O device(s) 172. The I/O interface(s) 170 may enable information to be transferred in or out of the system 160, or between components of the system 160, through serial communication, parallel communication, or other types of communication. For example, the I/O interface(s) 170 may comply with a version of the RS-232 standard for serial ports, or with a version of the IEEE 1284 standard for parallel ports. As another example, the I/O interface(s) 170 may be configured to provide a connection over Universal Serial Bus (USB) or Ethernet. In some examples, the I/O interface(s) 170 may be configured to provide a serial connection that is compliant with a version of the IEEE 1394 standard.

The I/O interface(s) 170 may also include one or more network interfaces that enable communications between computing devices in the system 160, or between the system 160 and other network-connected computing systems. The network interface(s) may include one or more network interface controllers (NICs) or other types of transceiver devices configured to send and receive communications over one or more networks using any network protocol.

Computing devices of the system 160 may communicate with one another, or with other computing devices, using one or more networks. Such networks may include public networks such as the internet, private networks such as an institutional or personal intranet, or any combination of private and public networks. The networks may include any type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In some implementations, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 160 may include any number of computing devices of any type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), implementations are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

The term data processing apparatus (also referred to herein as a data processing system) refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a standalone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a data communication network.

In this specification, the term database is used broadly to refer to any collection of data: the data does not need to be structured in any particular way, or structured at all, and it can be stored on storage devices in one or more locations. Thus, for example, the index database can include multiple collections of data, each of which may be organized and accessed differently.

Similarly, in this specification the term engine is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially be claimed as such, one or more features from a claimed combination can in some cases be excised from the combination, and the claimed combination may be directed to a sub-combination or variation of a sub-combination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method implemented by a computer system for detecting personally identifiable information (PII) in clinical trial data before the clinical trial data is committed to a hardware storage device to improve data security, comprising:

causing rendering, by a computer system, of a graphical user interface with one or more input portions for input of clinical trial data and one or more controls;

responsive to selection of at least one of the one or more controls, receiving, by the computer system through the graphical user interface, clinical trial data input into at least one of the one or more input portions of the graphical user interface;

prior to committing the clinical trial data to a hardware storage device, associating, in memory, the clinical trial data input into at least one of the one or more input portions of the graphical user interface with a pending state;

training a machine learning model to detect personally identifiable information (PII) using a learning technique based on training data received as input, wherein the machine learning model is configured to receive as input clinical trial data and to process the input clinical trial data to generate an output that specifies whether the clinical trial data includes PII, wherein the machine learning model comprises a plurality of artificial neurons that are connected through edges and are aggregated into a plurality of layers comprising at least an input layer and an output layer, wherein each of the edges is configured to transmit a signal from one artificial neuron to another artificial neuron, and wherein an output of each of the plurality of artificial neurons is computed by a specified function of a sum of inputs of the artificial neuron in accordance with a plurality of weights;

adjusting values of the plurality of weights based on the training of the machine learning model;

processing, by the computer system, clinical trial data using the plurality of artificial neurons in the trained machine learning model in accordance with the values of the plurality of weights to detect, by the trained machine learning model, whether the clinical trial data includes PII;

at least partly based on an output of the machine learning model, determining whether the clinical trial data includes PII;

upon determining that the clinical trial data does not include PII, accessing, from memory, the clinical trial data input into at least one of the one or more input portions of the graphical user interface and associated with the pending state;

releasing the clinical trial data from the pending state; and committing the clinical trial data released to the hardware storage device.

2. The method of claim 1, further comprising:

receiving, from the machine learning model, an indication that the clinical trial data does not include PII.

3. The method of claim 1, further comprising:

receiving, from the machine learning model, an indication that the clinical trial data includes PII;

causing rendering an overlay in the graphical user interface, with the rendered overlay displaying a notification of the detected PII and further displaying:

a first prompt to confirm that the clinical trial data does not include PII, with the first prompt being juxtaposed to the notification in the overlay; and a second prompt to update the clinical trial data to not include PII, with the second prompt being juxtaposed to the notification in the overlay.

4. The method of claim 3, further comprising:

receiving data confirming that the clinical trial data does not include PII.

5. The method of claim 3, wherein the overlay is a first overlay, the method further comprising:

a) receiving, by the computer system through the graphical user interface, an update to the input clinical trial data;

b) prior to committing the update to the input clinical trial data to the hardware storage device, associating, in memory, the update to the clinical trial data with a pending state indictor;

c) causing, by the computer system, the machine learning model to detect whether the update to the input clinical trial data includes PII;

d) when the machine learning model detects that the update to the input clinical trial data includes PII, rendering a second overlay in the graphical user interface, with the rendered second overlay displaying another notification of the detected PII and further displaying:

a first prompt to confirm that the update to the clinical trial data does not include PII, with the first prompt being juxtaposed to the other notification in the second overlay; and a second prompt to update the updated clinical trial data to not include PII, with the second prompt being juxtaposed to the other notification in the second overlay;

e) repeating steps a-d until confirmation is received that an update to the clinical trial data does not include PII or until the machine learning model detects an absence of PII, once confirmation is received that the update to the clinical trial data does not include PII or the machine learning model detects an absence of PII, committing a most recently submitted update to the input clinical trial data to the hardware storage device.

6. The method of claim 1, wherein the machine learning model is a large language model (LLM), the method further comprising:

generating a system prompt to guide the LLM to interpret input corresponding to the clinical trial data input into at least one of the one or more input portions of the graphical user interface and to provide a specified type of output; and inputting, into the LLM, the system prompt and the input corresponding to the clinical trial data input into at least one of the one or more input portions of the graphical user interface.

7. The method of claim 1, wherein committing includes:

creating an entry in a specified table in the hardware storage device, with data corresponding to the input clinical trial data being saved in the created entry; and creating an entry in an audit trail table to track modifications to the input clinical trial data or to data corresponding to the input clinical trial data.

8. The method of claim 1, wherein committing the clinical trial data to the hardware storage device includes committing data corresponding to the clinical trial data to the hardware storage device.

9. A data processing system for detecting personally identifiable information (PII) in clinical trial data before the clinical trial data is committed to a hardware storage device to improve data security, comprising:

one or more processing devices; and one or more machine-readable hardware storage devices storing instructions that are executable by the one or more processing devices to perform operations comprising:

causing rendering of a graphical user interface with one or more input portions for input of clinical trial data and one or more controls;

responsive to selection of at least one of the one or more controls, receiving, through the graphical user interface, clinical trial data input into at least one of the one or more input portions of the graphical user interface;

prior to committing the clinical trial data to a hardware storage device, associating, in memory, the clinical trial data input into at least one of the one or more input portions of the graphical user interface with a pending state;

training a machine learning model to detect personally identifiable information (PII) using a learning technique based on training data received as input, wherein the machine learning model is configured to receive as input clinical trial data and to process the input clinical trial data to generate an output that specifies whether the clinical trial data includes PII, wherein the machine learning model comprises a plurality of artificial neurons that are connected through edges and are aggregated into a plurality of layers comprising at least an input layer and an output layer, wherein each of the edges is configured to transmit a signal from one artificial neuron to another artificial neuron, and wherein an output of each of the plurality of artificial neurons is computed by a specified function of a sum of inputs of the artificial neuron in accordance with a plurality of weights;

adjusting values of the plurality of weights based on the training of the machine learning model;

processing clinical trial data using the plurality of artificial neurons in the trained machine learning model in accordance with the values of the plurality of weights to detect, by the trained machine learning model, whether the clinical trial data includes PII;

at least partly based on an output of the machine learning model, determining whether the clinical trial data includes PII;

upon determining that the clinical trial data does not include PII, accessing, from memory, the clinical trial data input into at least one of the one or more input portions of the graphical user interface and associated with the pending state;

releasing the clinical trial data from the pending state; and committing the clinical trial data released to the hardware storage device.

10. The data processing system of claim 9, wherein the operations further comprise:

receiving, from the machine learning model, an indication that the clinical trial data does not include PII.

11. The data processing system of claim 9, wherein the operations further comprise:

receiving, from the machine learning model, an indication that the clinical trial data includes PII;

causing rendering an overlay in the graphical user interface, with the rendered overlay displaying a notification of the detected PII and further displaying:

a first prompt to confirm that the clinical trial data does not include PII, with the first prompt being juxtaposed to the notification in the overlay; and a second prompt to update the clinical trial data to not include PII, with the second prompt being juxtaposed to the notification in the overlay.

12. The data processing system of claim 11, wherein the operations further comprise:

receiving data confirming that the clinical trial data does not include PII.

13. The data processing system of claim 11, wherein the overlay is a first overlay, wherein the operations further comprise:

a) receiving, through the graphical user interface, an update to the input clinical trial data;

b) prior to committing the update to the input clinical trial data to the hardware storage device, associating, in memory, the update to the clinical trial data with a pending state indictor;

c) causing the machine learning model to detect whether the update to the input clinical trial data includes PII;

d) when the machine learning model detects that the update to the input clinical trial data includes PII, rendering a second overlay in the graphical user interface, with the rendered second overlay displaying another notification of the detected PII and further displaying:

a first prompt to confirm that the update to the clinical trial data does not include PII, with the first prompt being juxtaposed to the other notification in the second overlay; and a second prompt to update the updated clinical trial data to not include PII, with the second prompt being juxtaposed to the other notification in the second overlay;

e) repeating steps a-d until confirmation is received that an update to the clinical trial data does not include PII or until the machine learning model detects an absence of PII, once confirmation is received that the update to the clinical trial data does not include PII or the machine learning model detects an absence of PII, committing a most recently submitted update to the input clinical trial data to the hardware storage device.

14. The data processing system of claim 9, wherein the machine learning model is a large language model (LLM), and wherein the operations further comprise:

generating a system prompt to guide the LLM to interpret input corresponding to the clinical trial data input into at least one of the one or more input portions of the graphical user interface and to provide a specified type of output; and inputting, into the LLM, the system prompt and the input corresponding to the clinical trial data input into at least one of the one or more input portions of the graphical user interface.

15. The data processing system of claim 9, wherein committing includes:

creating an entry in a specified table in the hardware storage device, with data corresponding to the input clinical trial data being saved in the created entry; and creating an entry in an audit trail table to track modifications to the input clinical trial data or to data corresponding to the input clinical trial data.

16. The data processing system of claim 9, wherein committing the clinical trial data to the hardware storage device includes committing data corresponding to the clinical trial data to the hardware storage device.

17. A non-transitory computer readable medium for detecting personally identifiable information (PII) in clinical trial data before the clinical trial data is committed to a hardware storage device to improve data security, the non-transitory computer readable medium storing instructions that are executable by one or more processing devices to perform operations comprising:

causing rendering of a graphical user interface with one or more input portions for input of clinical trial data and one or more controls;

responsive to selection of at least one of the one or more controls, receiving, through the graphical user interface, clinical trial data input into at least one of the one or more input portions of the graphical user interface;

prior to committing the clinical trial data to a hardware storage device, associating, in memory, the clinical trial data input into at least one of the one or more input portions of the graphical user interface with a pending state;

training a machine learning model to detect personally identifiable information (PII) using a learning technique based on training data received as input, wherein the machine learning model is configured to receive as input clinical trial data and to process the input clinical trial data to generate an output that specifies whether the clinical trial data includes PII, wherein the machine learning model comprises a plurality of artificial neurons that are connected through edges and are aggregated into a plurality of layers comprising at least an input layer and an output layer, wherein each of the edges is configured to transmit a signal from one artificial neuron to another artificial neuron, and wherein an output of each of the plurality of artificial neurons is computed by a specified function of a sum of inputs of the artificial neuron in accordance with a plurality of weights;

adjusting values of the plurality of weights based on the training of the machine learning model;

processing, by the computer system, clinical trial data using the plurality of artificial neurons in the trained machine learning model in accordance with the values of the plurality of weights to detect, by the trained machine learning model, whether the clinical trial data includes PII;

at least partly based on an output of the machine learning model, determining whether the clinical trial data includes PII;

upon determining that the clinical trial data does not include PII, accessing, from memory, the clinical trial data input into at least one of the one or more input portions of the graphical user interface and associated with the pending state;

releasing the clinical trial data from the pending state; and committing the clinical trial data released to the hardware storage device.

18. The non-transitory computer readable medium of claim 17, wherein the operations further comprise:

receiving, from the machine learning model, an indication that the clinical trial data does not include PII.

19. The non-transitory computer readable medium of claim 17, wherein the operations further comprise:

receiving, from the machine learning model, an indication that the clinical trial data includes PII;

causing rendering an overlay in the graphical user interface, with the rendered overlay displaying a notification of the detected PII and further displaying:

a first prompt to confirm that the clinical trial data does not include PII, with the first prompt being juxtaposed to the notification in the overlay; and a second prompt to update the clinical trial data to not include PII, with the second prompt being juxtaposed to the notification in the overlay.

20. The non-transitory computer readable medium of claim 19, wherein the operations further comprise:

receiving data confirming that the clinical trial data does not include PII.

* * * * *